United States Patent
Zhu et al.

(10) Patent No.: US 12,020,786 B2
(45) Date of Patent: Jun. 25, 2024

(54) MODEL FOR HEALTH RECORD CLASSIFICATION

(71) Applicant: Apixio, LLC, San Mateo, CA (US)

(72) Inventors: John Zhu, San Mateo, CA (US); Noah Lieberman, San Francisco, CA (US); Ha Pham, Los Altos, CA (US); Vishnuvyas Sethumadhavan, Mountain View, CA (US)

(73) Assignee: Apixio, LLC, San Mateo, CA (US)

( * ) Notice: Subject to any disclaimer, the term of this patent is extended or adjusted under 35 U.S.C. 154(b) by 427 days.

(21) Appl. No.: 16/869,560

(22) Filed: May 7, 2020

(65) Prior Publication Data

US 2020/0356825 A1 Nov. 12, 2020

Related U.S. Application Data (60) Provisional application No. 62/846,555, filed on May 10, 2019.

(51) Int. Cl.
| | |
|---|---|
| *G16H 10/60* | (2018.01) |
| *G06F 18/21* | (2023.01) |
| *G06F 18/231* | (2023.01) |
| *G06F 18/2413* | (2023.01) |
| *G06V 30/413* | (2022.01) |
| *G16H 15/00* | (2018.01) |
| *G16H 40/20* | (2018.01) |
| *G16H 50/20* | (2018.01) |
| *G16H 50/70* | (2018.01) |

(52) U.S. Cl.
CPC ......... *G16H 10/60* (2018.01); *G06F 18/2178* (2023.01); *G06F 18/231* (2023.01); *G06F 18/24147* (2023.01); *G06V 30/413* (2022.01); *G16H 15/00* (2018.01); *G16H 40/20* (2018.01); *G16H 50/20* (2018.01); *G16H 50/70* (2018.01)

(58) Field of Classification Search
CPC .... G06K 9/6276; G06K 9/6219; G06K 9/626; G16H 40/20; G16H 10/60; G16H 15/00; G16H 50/70; G16H 50/20; G06V 30/413
USPC .......................................................... 705/3
See application file for complete search history.

(56) References Cited

U.S. PATENT DOCUMENTS

| | | | |
|---|---|---|---|
| 2014/0108047 A1* | 4/2014 | Kinney | G16H 10/60 705/3 |
| 2015/0025908 A1* | 1/2015 | Lakshminarayan | G16H 10/60 705/3 |
| 2020/0111545 A1* | 4/2020 | Syeda-Mahmood | G16H 50/70 |

FOREIGN PATENT DOCUMENTS

CN 107833603 A * 3/2018 ........... G06K 9/6267

OTHER PUBLICATIONS

Nutakki, G. C., Nasraoui, O., Abdollahi, B., Badami, M., & Sun, W. (Jan. 2014). Distributed lda-based topic modeling and topic agglomeration in a latent space. In SNOW-DC@ WWW. (Year: 2014).*

(Continued)

*Primary Examiner* — Mamon Obeid
*Assistant Examiner* — Winston Furtado
(74) *Attorney, Agent, or Firm* — Armstrong Teasdale LLP (57) ABSTRACT

An electronic medical record (EMR) analysis machine automatically clusters electronic medical records to produce an initial EMR analysis model and to identify high-value EMR documents such that human analysts can focus effort on labeling only high-value EMR documents to iteratively and extremely efficiently train an EMR analysis model. High- (Continued)

value sample EMR documents are identified as those whose membership in one or more clusters is most ambiguous, i.e., nearest the cluster boundary.

18 Claims, 9 Drawing Sheets

(56) References Cited

OTHER PUBLICATIONS

Meystre, S. M., Friedlin, F. J., South, B. R., Shen, S., & Samore, M. H. (2010). Automatic de-identification of textual documents in the electronic health record: a review of recent research. BMC medical research methodology, 10(1), 1-16. (Year: 2010).*

Brücher, H., Knolmayer, G., & Mittermayer, M. A. (2002). Document classification methods for organizing explicit knowledge. (Year: 2002).*

* cited by examiner

MODEL FOR HEALTH RECORD CLASSIFICATION

CROSS REFERENCE TO RELATED APPLICATION

This application claims priority of U.S. Provisional Application Ser. No. 62/846,555 filed on May 10, 2019, of the same title, which is hereby fully incorporated by reference.

FIELD OF THE INVENTION

The present invention relates generally to health record analysis, and, more particularly, to a computer-implemented health record classification tool with significantly improved accuracy and efficacy.

BACKGROUND OF THE INVENTION

Despite rapid growth of innovation in other fields in recent decades, the world of medical information—including patient medical records, billing, and a host of other information—has enjoyed little to no useful consolidation, reliability, or ease-of-access. This has left medical professionals, hospitals, clinics, and even insurance companies with many challenges, such as unreliability of medical information, uncertainty of diagnoses, and numerous other problems stemming from the inaccessibility of the large body of medical information stored somewhere.

One of the challenges facing those in the medical or related areas is the number of sources of information, the great amount of information from each source, and the lack of consolidation of such information in a manner that renders it meaningful and useful. This has resulted in medical costs much greater than should be needed.

Currently, when a patient sees various medical professionals over the years, there is no method for universally tracking recommendations, thoughts, prescriptions, diagnosis. This hinders insurance companies in making certain requisite determinations, physicians in making decisions that directly affect the health of the patient, and hospitals and other medical institutions in making decisions regarding the care of patients.

Electronic medical records (EMR) are growing at an exponential rate. In 2012, it was estimated that thirty percent (30%) of all the electronic data storage in the world was occupied by the healthcare industry. Much, if not all, of this information is in formats specific to a given medical practice and not easily categorized and analyzed across multiple medical practices. Since the amount of EMR data is growing exponentially, manual classification and categorization and generally any organization of such data is simply impossible. However, such classification, categorization, and organization is essential to providing improved care.

Machine classification and categorization requires very large amounts of high quality labeled data. However, the mountainous body of EMR data that is to be classified and categorized comes from many disparate sources and is largely unlabeled or, at best, poorly labeled and generally not labeled consistently across the disparate sources. As a result, conventional machine learning and artificial intelligence techniques are useless until a significant portion of the mountainous body of EMR data can be accurately and consistently labeled.

What is needed is a way to automate labeling, classification, categorization, and organization of the gargantuan, mountainous body of stored EMR data that continues to grow exponentially.

SUMMARY OF THE INVENTION

In accordance with the present invention, an electronic medical record (EMR) analysis machine automatically clusters electronic medical records to produce an initial EMR analysis model and to identify high-value EMR documents such that human analysts can focus effort on labeling only high-value EMR documents to iteratively and extremely efficiently train an EMR analysis model. High-value sample EMR documents are identified as those whose membership in one or more clusters is most ambiguous, i.e., nearest the cluster boundary.

Ordinarily, the gargantuan, mountainous, exponentially growing body of stored EMR data is simply too large for effective model training as model training requires human intervention. Current machine learning techniques still require millions upon millions of sample EMR documents that are properly labeled by human analysts. For example, to build a model that can distinguish EMR data for patients who have had a heart attack from EMR data for patients who haven't, a substantial body of EMR data must be analyzed by human analysts to properly label the EMR data as indicating a heart attack or as indicating no heart attack before this body of EMR data can be used to train the model.

However, by having a machine cluster the EMR data, EMR data near cluster boundaries can be identified as particularly important in training the model and expensive human analyst time and resources can be used to only label this high-value EMR data. As a result, the EMR data analysis model can be trained much more efficiently.

A BRIEF DESCRIPTION OF THE DRAWINGS

In order that the present invention may be more clearly ascertained, some embodiments will now be described, by way of example, with reference to the accompanying drawings, in which.

DETAILED DESCRIPTION OF THE INVENTION

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

Aspects, features and advantages of exemplary embodiments of the present invention will become better understood with regard to the following description in connection with the accompanying drawing(s). It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. Hence, use of absolute and/or sequential terms, such as, for example, "will," "will not," "shall," "shall not," "must," "must not," "first," "initially," "next," "subsequently," "before," "after," "lastly," and "finally," are not meant to limit the scope of the present invention as the embodiments disclosed herein are merely exemplary.

In accordance with the present invention, an electronic medical record (EMR) analysis machine 102 (FIG. 1) analyzes electronic medical records 104 to produce an EMR analysis model 106 for efficiently, accurately, and automatically analyze EMR documents of EMR 104. EMR analysis machine 102 builds EMR analysis model 106 by (i) clustering EMR documents according to terms and topics and selecting EMR documents nearest to and furthest from centers of the clusters as training data and (ii) iteratively training EMR analysis model 106 using the selected training data.

Figure 2:
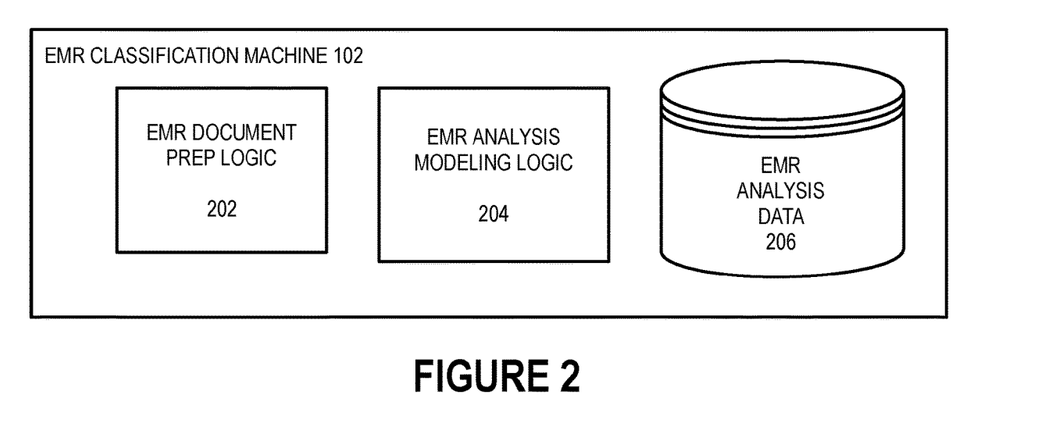
FIG. 2 is a block diagram of the EMR document classification machine of FIG. 1 in greater detail.

EMR analysis machine 102 is shown in greater detail in FIG. 2 and includes EMR document prep logic 202, EMR analysis modeling logic 204, and EMR analysis data 206, which includes EMR analysis model 106. In a manner described more completely below, EMR document prep logic 202 processes EMR documents of EMR 104 to derive EMR document metadata that is used by EMR analysis modeling logic 204 in producing and training EMR analysis model 106. The EMR document metadata produced by EMR document prep logic 202 is stored in EMR analysis data 206. Also in a manner described more completely below, EMR analysis modeling logic 204 trains EMR analysis model 106 using records selected from EMR 104 according to the EMR document metadata.

Figure 3:
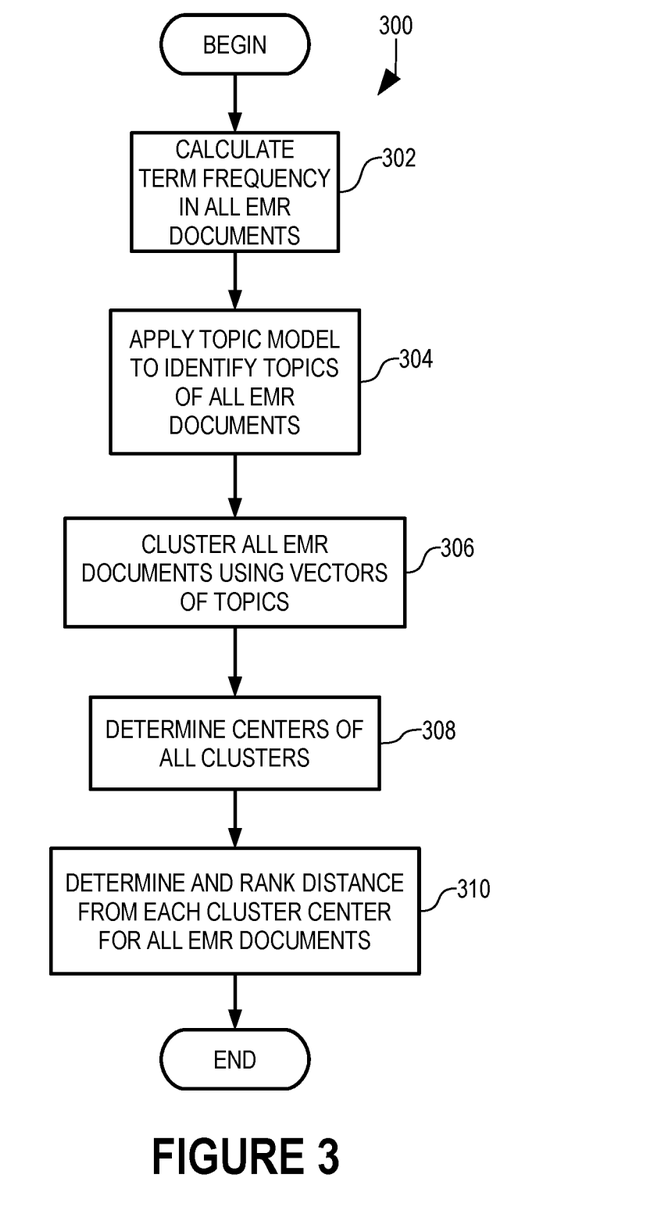
FIG. 3 is a logic flow diagram illustrating the preparation of EMR documents for classification in accordance with the present invention.

EMR document prep logic 202 processes EMR documents of EMR 104 to cluster those EMR documents so that high-value EMR documents can be identified in the manner described below for exceptionally efficient training of EMR analysis model 106. The process by which EMR document prep logic 202 processes EMR documents of EMR 104 to derive EMR document metadata is illustrated by logic flow diagram 300 (FIG. 3).

In step 302, EMR document prep logic 202 calculates frequency of each of a number of predetermined terms in EMR documents of EMR 104. EMR 104 is shown in greater detail in FIG. 4 and includes a number of patient records 402, each of which includes a number of EMR documents 404. EMR documents such as EMR documents 404 are conventional and known.

Figure 4:
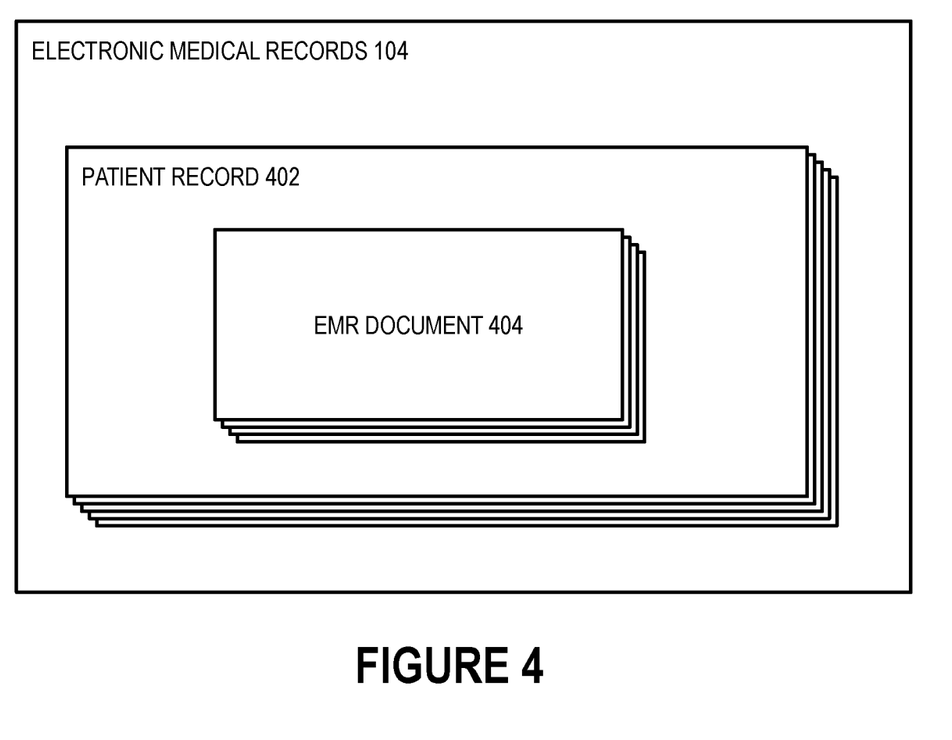
FIG. 4 is a block diagram of EMR documents of FIG. 1 in greater detail.
Figure 5:
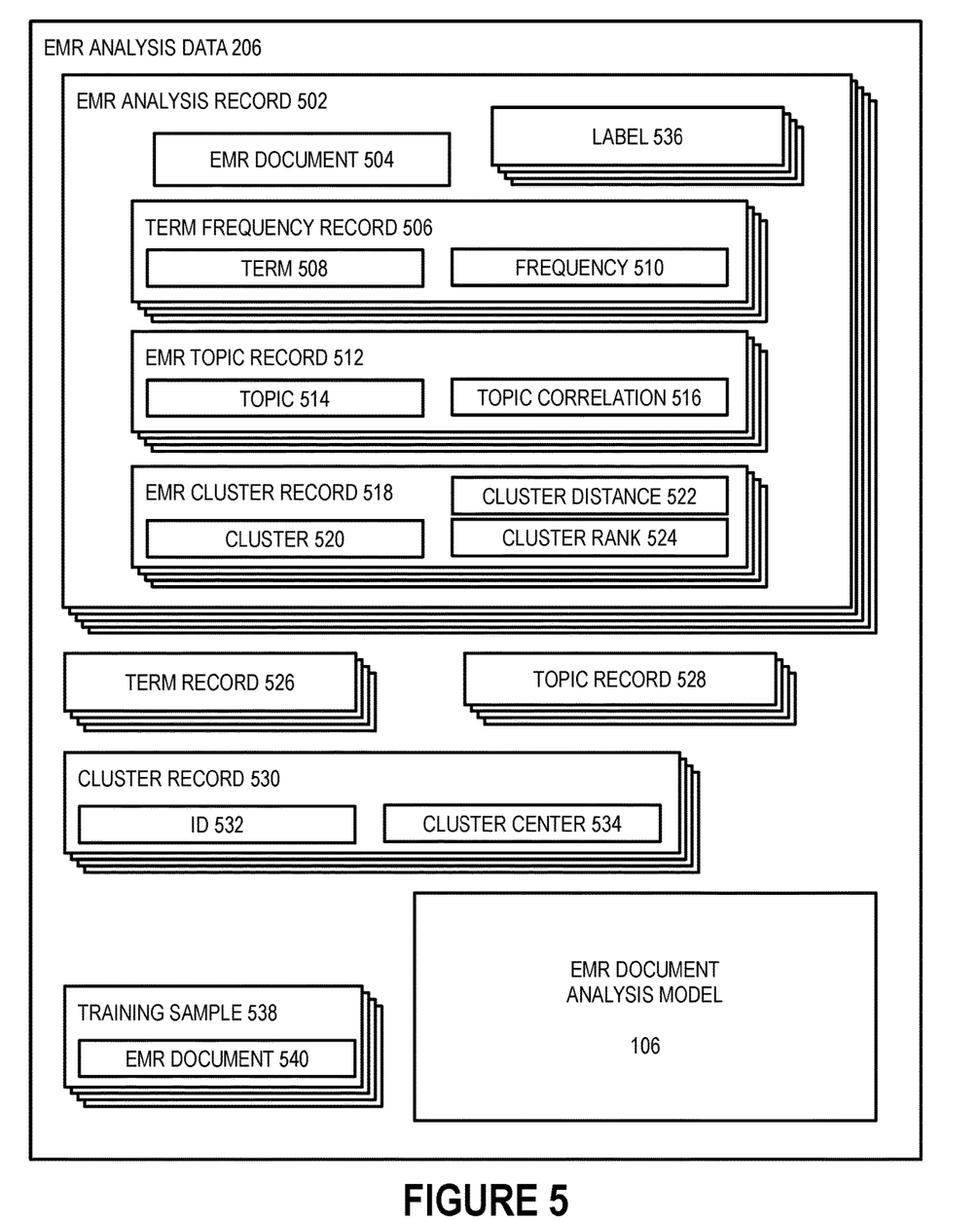
FIG. 5 is a block diagram of EMR analysis data used by the EMR document classification machine of FIG. 2.

EMR analysis data 206 (FIG. 2) is shown in greater detail in FIG. 5 and includes a number of term records 526, each of which specifies a term of interest in EMR documents such as EMR documents 404 (FIG. 4). Each of the EMR documents processed by EMR document prep logic 202 is represented by an EMR analysis record 502. The particular one of EMR documents 404 represented by EMR analysis record 502 is identified by EMR document 504 and is sometimes referred to as the subject EMR document. Each of term frequency records 506 corresponds to a respective one of term records 526, term 508 identifying the term and frequency 510 representing the frequency of the term in the subject EMR document. In this illustrative embodiment, EMR document prep logic 206 calculates frequency 510 using TF-IDF (term frequency-inverse document frequency) analysis.

In step 304 (FIG. 3), EMR document prep logic 202 applies a topic model to identify topics present in all EMR documents of EMR 104. In this illustrative embodiment, the particular topic model applied by EMR document prep logic 202 is a latent Dirichlet allocation (LDA) topic model. EMR document prep logic 202 uses terms 508 and frequencies 510 of term frequency records 506 of the various EMR documents to identify topics and respective strengths of correlation to the topics. EMR document prep logic 202 stores topics and respective correlations in topic 514 and topic correlation 516 of an EMR topic record 512. EMR document prep logic 202 stores each unique topic identified by application of the topic model as a corresponding one of topic records 528. Topic records 528 can be manually augmented with descriptions of the topics entered by human system operators. Such descriptions can be helpful in forming label 536 for supervised training in the manner described below.

In step 306 (FIG. 3), EMR document prep logic 202 clusters all EMR documents 404 (FIG. 4) using vectors of EMR topic records 512. Using topics rather than term frequencies as a vector for clustering significantly improves the efficiency of clustering. Specifically, unique terms of term records 526 can number in the millions whereas unique topics of topic records 528 typically number in the few thousands. Clustering vectors of a few thousand dimensions is far more efficient than clustering vectors of millions of dimensions. In this illustrative embodiment, EMR document prep logic 202 clusters the EMR document around the topics of topic records 528 using known bisecting K-means techniques.

The result of clustering by EMR document prep logic 202 in step 306 is a number of unique clusters represented by cluster records 530, each of which has a unique cluster identifier 532. In addition, membership of each of EMR documents 404 is represented by an EMR cluster record 518 with a cluster identifier 520 that corresponds to one of cluster identifiers 532.

In step 308 (FIG. 3), EMR document prep logic 202 calculates the center of each cluster according to the topic vectors of the constituent EMR documents of each cluster. EMR document prep logic 202 stores the center of the cluster as cluster center 534 for each of cluster records 530. Each of cluster centers 534 is a vector in the multi-dimensional space of the topic vectors of EMR analysis records 502 represented by EMR topic records 506.

In step 310 (FIG. 3), for each EMR document represented by EMR analysis records 520, EMR document prep logic 202 calculates a cluster distance 522 from cluster center 534 of the corresponding cluster record 530 and a cluster rank 524. EMR document prep logic 202 calculates cluster distance 522 as a euclidean distance from cluster center 534. Cluster rank 524 represents a ranking of EMR document 504 in distance from cluster center 534 from nearest to furthest.

After step 310, processing by EMR document prep logic 202 according to logic flow diagram 300 completes. The result is that EMR documents are grouped into topic-based clusters and a distance from the cluster center for each EMR document is known.

Figure 6:
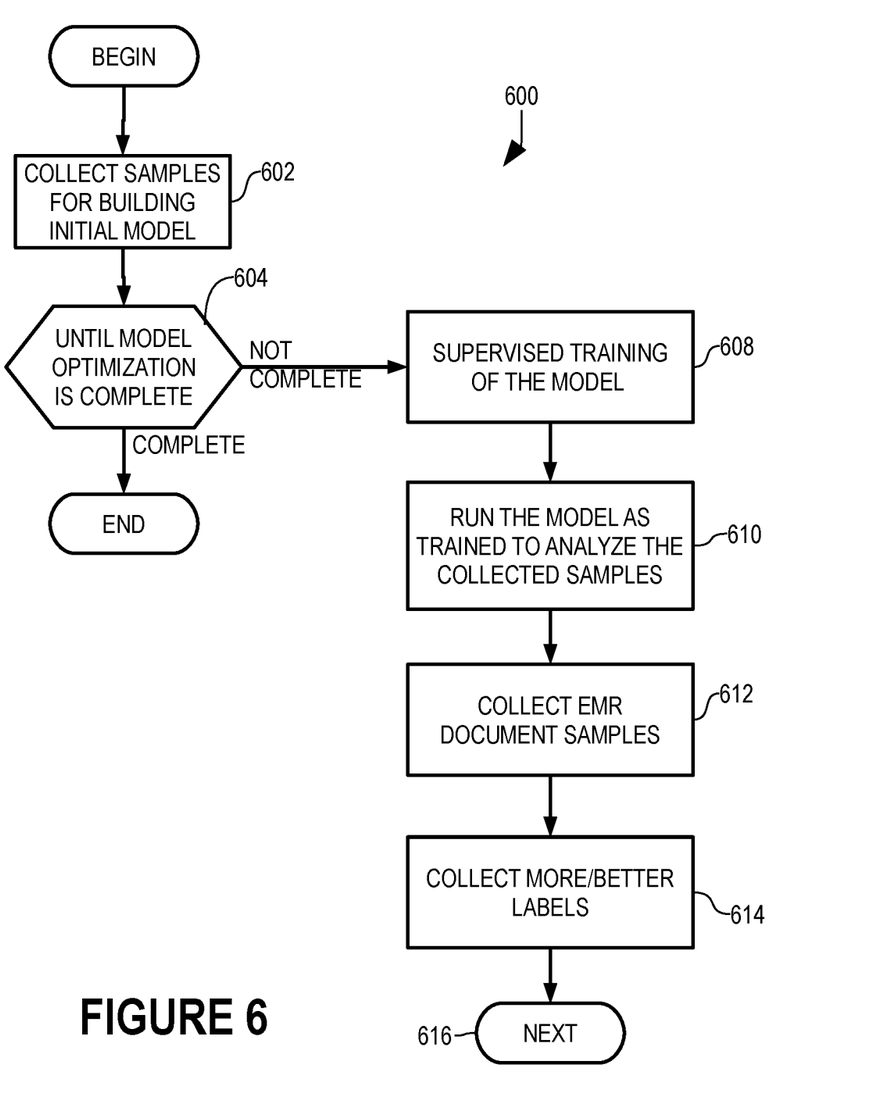
FIG. 6 is a logic flow diagram illustrating the training and optimization of an EMR document classification model by the EMR document classification machine of FIG. 3 in accordance with the present invention.

The EMR documents so clustered and prepared are used by EMR analysis modeling logic 204 to produce and train EMR analysis model 106 in a manner illustrated by logic flow diagram 600 (FIG. 6). EMR analysis modeling logic 204 trains EMR analysis model 106 according to parameters of a specific inquiry, i.e., according to machine learning labels specified by the particular analysis desired of the EMR documents. For example, the desired analysis can be to identify all patients whose EMR documents indicate that they've had a specific type of cancer or another medical condition or diagnosis. The particular inquiry or analysis determines the labels for which EMR analysis model 106 is trained.

Figure 7:
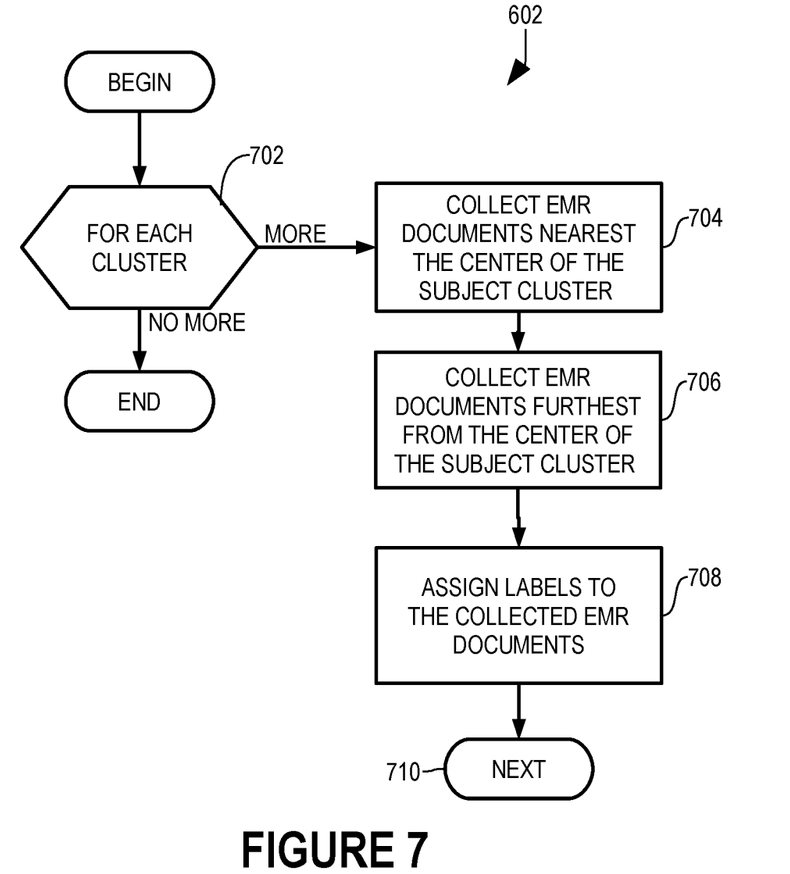
FIGS. 7-9 are each a logic flow diagram of a respective step of FIG. 6 in greater detail.

In step 602, EMR analysis modeling logic 204 collects samples from EMR analysis records 502 from which to build an initial model. Step 602 is shown in greater detail as logic flow diagram 602 (FIG. 7).

Loop step 702 and next step 710 define a loop in which EMR analysis modeling logic 204 processes each of cluster records 530 according to steps 704-708. In each iteration of the loop of steps 702-7108, the particular one of cluster records 530 processed by EMR analysis modeling logic 204 is sometimes referred to as the subject cluster.

In step 704, EMR analysis modeling logic 204 selects a number of EMR analysis records 502 (FIG. 5) for which cluster rank 524 is the highest. EMR analysis records 502 (FIG. 5) with the greatest distance from the cluster center are those whose membership in the cluster is least likely. In one embodiment, EMR analysis modeling logic 204 selects 300 of the highest ranked EMR analysis records 502. EMR analysis modeling logic 204 stores data identifying the selected EMR analysis records 502 in training samples 538, each of which includes an EMR document 540 that identifies a corresponding one of EMR analysis records 502.

In step 706 (FIG. 7), EMR analysis modeling logic 204 selects a number of EMR analysis records 502 (FIG. 5) for which cluster rank 524 is the lowest. EMR analysis records 502 (FIG. 5) with the lowest distance from the cluster center are those whose membership in the cluster is most likely. In one embodiment, EMR analysis modeling logic 204 selects 300 of the lowest ranked EMR analysis records 502. As described above with respect to step 704, EMR analysis modeling logic 204 stores data identifying the selected EMR analysis records 502 in training samples 538, each of which includes an EMR document 540 that identifies a corresponding one of EMR analysis records 502.

In step 708 (FIG. 7), EMR analysis modeling logic 204 prompts human analysts to assign labels to the collected EMR documents. The manner in which EMR analysis modeling logic 204 is described below in conjunction with step 614 (FIG. 6).

Processing by EMR analysis modeling logic 204 transfers through next step 710 to loop step 702 and EMR analysis modeling logic 204 processes the another of cluster records 530. Once EMR analysis modeling logic 204 has processed all of cluster records 530 according to the loop of steps 702-710, processing according to logic flow diagram 602, and therefore step 602 (FIG. 6), completes.

Loop step 604 and next step 616 define a loop in which EMR analysis modeling logic 204 repeated performs steps 608-614 until EMR document analysis model 106 is sufficiently optimized. In this illustrative embodiment, EMR document classification model 106 is sufficiently optimized when additional performances of the loop of steps 604-616 do not produce significantly different results.

In step 608, EMR analysis modeling logic 204 trains EMR document classification model 106 using the collected samples represented by training samples 538. In the first performance of step 608 by EMR analysis modeling logic 204, training samples 538 are collected in step 602 as described above. In subsequent performances of step 608, training samples 538 are collected in step 612 as described below. In this illustrative embodiment, EMR analysis modeling logic 204 performs supervised training of EMR document analysis model 106, including interaction with a human analyst who supervises the training of step 610.

As described above with respect to step 602, the initial set of training samples 538 includes, for each cluster, EMR analysis records 502 that are solidly in the cluster and EMR analysis records 502 that are barely in the cluster. Accordingly, training EMR document classification model 106 in the first performance of step 608 measures, to a fairly large degree, correlations between the clusters and the labels of the particular analysis for which EMR analysis model 106 is being built and weights within EMR analysis model 106 initially reflect those correlations. However, since the clusters are constructed automatically without reference to the labels, the clusters may or may not correlate strongly with those labels. This initial training simply provides a starting point from which EMR analysis model 106 can be iteratively improved in the loop of steps 604-616.

In step 610, EMR analysis modeling logic 204 runs EMR document analysis model 106 as trained to analyze EMR analysis records 502 (FIG. 5). In some embodiments, the model is "exported" in a standardized format to run on a production system. The production system has been built to host models. The models can be multiple standard model types, such as regressions, deep learning and the like. The models may be specializations of the architecture with their own formats and runtime inferencing infrastructure. The formatting of these very different models into a standardized format enables them to be seamlessly integrated into the host system regardless of the original format and runtime infrastructure.

Figure 8:
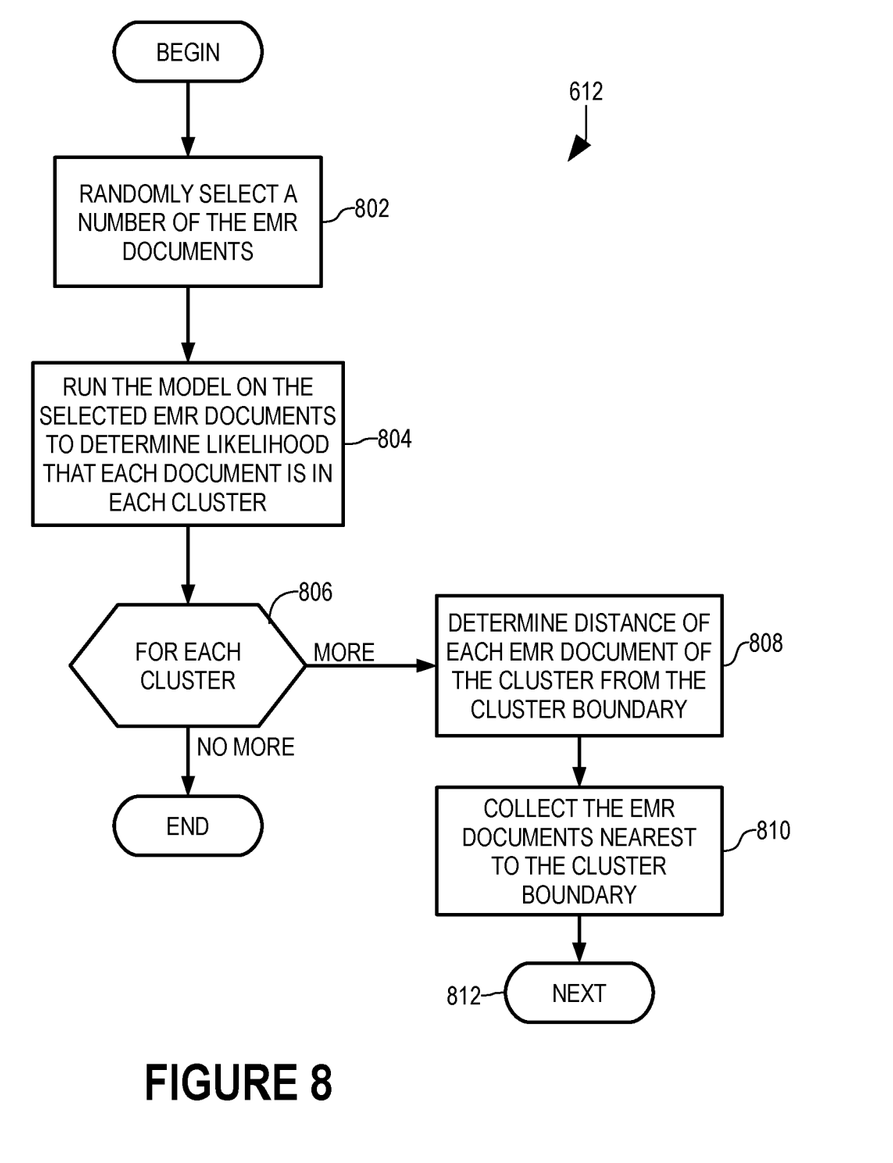

In step 612, EMR analysis modeling logic 204 uses the results of EMR document classification model 106, collects EMR analysis records 502 as a new set of training samples 538, replacing the previously collected training samples 538. In particular, EMR analysis modeling logic 204 gathers high-quality samples 538 of EMR analysis records 502, i.e., samples 538 that are most likely to provide the greatest improvement of EMR analysis model 106 when used to train EMR analysis model 106. Step 612 is shown in greater detail as logic flow diagram 612 (FIG. 8).

In step 802, EMR analysis modeling logic 204 pseudo-randomly selects a number of EMR analysis records 502 as candidates for the new set of training samples 538. In this illustrative embodiment, EMR analysis records 502 are divided into numerous, relatively equal-sized partitions, each containing thousands of EMR analysis records 502. EMR analysis modeling logic 204 pseudo-randomly selects a number of EMR analysis records 502 by pseudo-randomly selecting a number of the partitions. The EMR documents of the EMR analysis records 502 selected in step 802 are sometimes referred to as the selected EMR documents.

In step 804, EMR analysis modeling logic 204 runs the model trained in step 608 on the selected EMR documents to determine, for each of the selected EMR documents, a likelihood that the EMR document is a member of each of the clusters represented by cluster records 530.

Loop step 806 and next step 812 define a loop in which EMR analysis modeling logic 204 processes each of the clusters represented by cluster records 530 according to steps 808-810. During each iteration of the loop of steps 806-812, the particular cluster processed by EMR analysis modeling logic 204 is sometimes referred to as the subject cluster.

In step 808, EMR analysis modeling logic 204 determines the distance of each of the selected EMR documents from the boundary of the subject cluster. In this illustrative embodiment, the boundary of the subject cluster is a likelihood of 0.5 that a given EMR document is a member of the cluster. Accordingly, the distance of an EMR document from the cluster boundary is the distance between 0.5 and the likelihood that the EMR document is a member of the cluster.

In step 810, EMR analysis modeling logic 204 identifies a number of the selected EMR documents nearest the cluster boundary and includes those identified EMR documents in the new set of training samples 538.

After step 810, processing by EMR analysis modeling logic 204 transfers through next step 812 to loop step 806 and EMR analysis modeling logic 204 processes the next cluster according to the loop of steps 806-812. When all clusters have been processed by EMR analysis modeling logic 204 according to the loop of steps 806-812, logic flow diagram 612, and therefore step 612 (FIG. 6), completes and selection of the new set of training samples 538 is complete.

Thus, in step 612, EMR analysis modeling logic 204 selects a number of EMR analysis records 502 whose membership in one or more clusters is most ambiguous. Training EMR analysis model 106 with these most ambiguous samples properly labeled (in step 614 below) provides the greatest improvement of EMR analysis model 106 in a single iteration of the loop of steps 604-616.

In step 614, EMR analysis modeling logic 204 collects more and/or better labels for training EMR document classification model 106. In this illustrative embodiment, collection of labels is accomplished by presenting each of the EMR analysis records 502 (FIG. 5) selected in step 612 to a number of human analysts and prompting the human analysts to specify a label for the EMR analysis record. For example, EMR analysis modeling logic 204 can accept a label for a given EMR document when at least a predetermined minimum majority agree as to the label, e.g., two out of three, three out of five, etc. If the predetermined minimum majority number of analysts agree to a label of the EMR document, e.g., does or does not indicate a heart attack, EMR analysis modeling logic 204 accepts the label and uses the EMR document so labeled in the next performance of training of EMR analysis model 106 in step 608 (FIG. 6).

Figure 9:
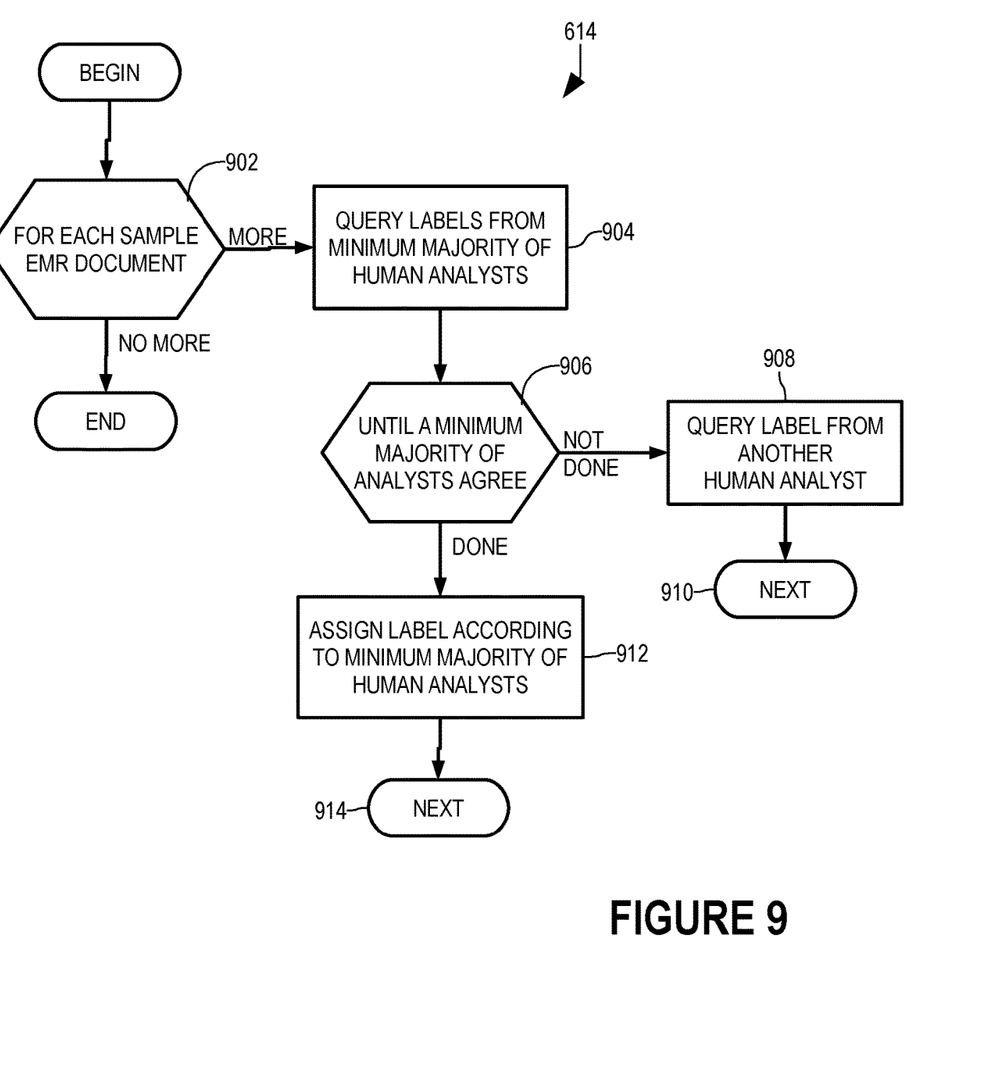
Figure 10:
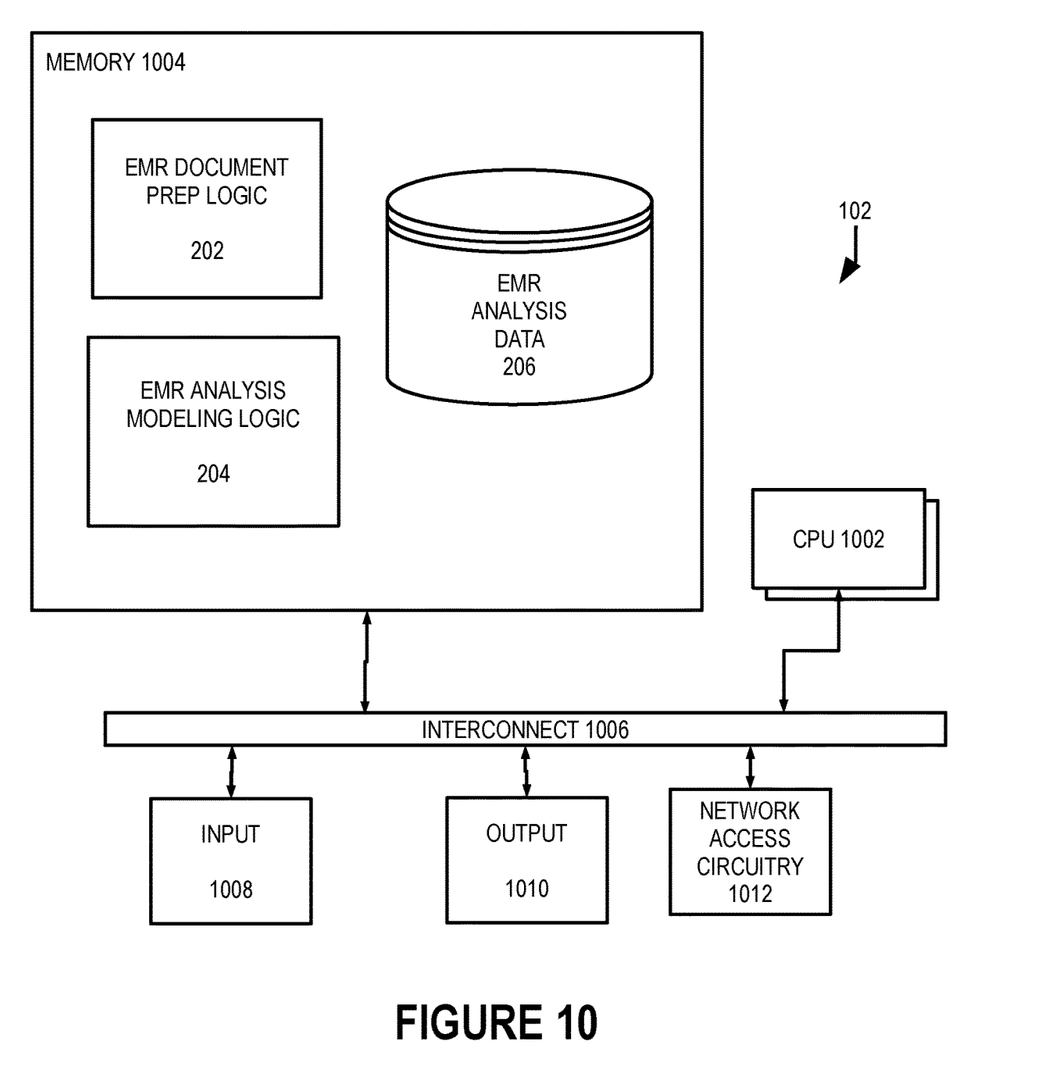
FIG. 10 is a block diagram of the EMR document classification machine of FIG. 1 in greater detail.

A particularly efficient embodiment of step 614 in the labeling of a given EMR document is shown as logic flow diagram 614 (FIG. 9). Loop step 902 and next step 914 define a loop in which EMR analysis modeling logic 204 processes each of the sample EMR analysis records 502 selected in step 612 according to steps 904-912. During an iteration of the loop of steps 902-914, the EMR document of the particular sample EMR analysis record 502 processed by EMR analysis modeling logic 204 is sometimes referred to as the subject EMR document.

In step 904, EMR analysis modeling logic 204 queries labels for the subject EMR document from the predetermined minimum majority number of human analysts. In this illustrative example, agreement among two of three human analysts is required for EMR analysis modeling logic 204 to accept a label, so the predetermined minimum majority is two. For three of five, the minimum majority would be three. For four of seven, the minimum majority would be four. And so on.

Loop step 906 and next step 910 define a loop in which EMR analysis modeling logic 204 performs step 908 until at least the predetermined minimum majority number of analysts agree. In step 908, EMR analysis modeling logic 204 queries a label for the subject EMR document from another human analyst. When at least the predetermined minimum majority number of analysts agree as to the labeling of the subject EMR document, processing according to the loop of steps 906-910 completes. It should be appreciated that additional analysts are queried only if the predetermined minimum majority has not yet been reached. For example, all analysts queried in step 904 agree regarding the labeling of the subject EMR document, step 908 is not performed.

After the loop of steps 906-610 completes, EMR analysis modeling logic 204 stores agreed-upon label, e.g., does or does not indicate a heart attack, in labels 536.

From step 912, processing by EMR analysis modeling logic 204 transfers through next step 914 to loop step 902 and the next of the selected sample EMR analysis records is processed according to the loop of steps 902-914. When all of the selected sample EMR analysis records is processed according to the loop of steps 902-914, processing according to logic flow diagram 614, and therefore step 614 (FIG. 6), completes.

From step 614, processing by EMR analysis modeling logic 204 transfers through next step 616 to loop step 604, and EMR analysis modeling logic 204 repeats processing according to steps 608-614. In the next iteration of the loop of steps 604-616, EMR analysis modeling logic 204 trains EMR analysis model 106 in step 608 using the labels assigned to high-value sample EMR documents, resulting in a significant improvement of EMR analysis model 106 with minimal involvement of human analysts.

EMR analysis machine 102 is shown in greater detail in FIG. 9. It should be appreciated that the behavior of EMR analysis machine 102 described herein can be distributed across multiple computer systems using conventional distributed processing techniques. EMR analysis machine 102 includes one or more microprocessors 1002 (collectively referred to as CPU 1002) that retrieve data and/or instructions from memory 1004 and execute retrieved instructions in a conventional manner. Memory 1004 can include generally any computer-readable medium including, for example, persistent memory such as magnetic and/or optical disks, ROM, and PROM and volatile memory such as RAM.

Figure 1:
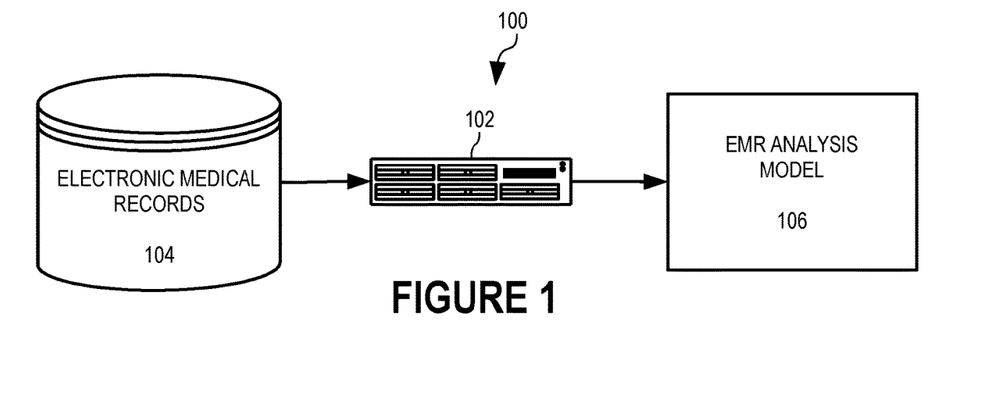
FIG. 1 shows an EMR document classification system in which an EMR document classification machine classifies EMR documents in accordance with the present invention.

CPU 1002 and memory 1004 are connected to one another through a conventional interconnect 1006, which is a bus in this illustrative embodiment and which connects CPU 1002 and memory 1004 to one or more input devices 1008, output devices 1010, and network access circuitry 1012. Input devices 1008 can include, for example, a keyboard, a keypad, a touch-sensitive screen, a mouse, a microphone, and one or more cameras. Output devices 1010 can include, for example, a display—such as a liquid crystal display (LCD)—and one or more loudspeakers. Network access circuitry 1012 sends and receives data through computer networks such as WAN 110 (FIG. 1). Server computer systems often exclude input and output devices, relying instead on human user interaction through network access circuitry. Accordingly, in some embodiments, health survey reliability analysis machine 102 does not include input devices 1008 and output devices 1010.

A number of components of EMR analysis machine 102 are stored in memory 1004. In particular, EMR document prep logic 202 and EMR analysis modeling logic 204 are each all or part of one or more computer processes executing within CPU 1002 from memory 1004 As used herein, "logic" refers to (i) logic implemented as computer instructions and/or data within one or more computer processes and/or (ii) logic implemented in electronic circuitry.

EMR analysis data 206 is data stored persistently in memory 1004 and can be implemented as all or part of one or more databases.

While this invention has been described in terms of several embodiments, there are alterations, modifications, permutations, and substitute equivalents, which fall within the scope of this invention. Although sub-section titles have been provided to aid in the description of the invention, these titles are merely illustrative and are not intended to limit the scope of the present invention.

It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. A method for building an electronic medical record (EMR) document analysis model implemented by at least one processor in communication with at least one memory, the method comprising:
    collecting EMR documents from a database;
    applying a latent Dirichlet allocation topic model to the EMR documents to generate cluster membership data comprising clusters associated with topics of the EMR documents, wherein one or more of the clusters comprises at least one thousand dimensions;
    storing the cluster membership data as metadata associated with the EMR documents;
    training the EMR document analysis model based on the clusters of the EMR documents and the metadata to produce a trained EMR document analysis model, wherein the clusters are based on the metadata and the topics associated therewith;
    applying the trained EMR document analysis model to the EMR documents to produce adjusted cluster membership data for each of the EMR documents, the adjusted cluster membership data comprising a ranking associated with a respective distance of each of the EMR documents from a respective center of the one or more clusters, wherein being within a first distance from the respective center indicates strong correlation to the one or more clusters and a lower ranking, wherein being outside the first distance from the respective center indicates a weak correlation to the one or more clusters and a higher ranking;
    updating the metadata based on the adjusted cluster membership;
    receiving an input that identifies a condition or diagnosis;
    creating labeled sample EMR documents by assigning EMR analysis labels associated with the condition or diagnosis to sample EMR documents, the sample EMR documents comprising EMR documents nearest a membership boundary of one or more of the clusters and outside the first distance from the respective center based on the updated metadata; and
    training the trained EMR document analysis model with the labeled sample EMR documents to produce an improved EMR document analysis model with respect to the condition or diagnosis, thereby producing the improved EMR document analysis model based on training the trained EMR document analysis model with the labeled sample EMR documents indicating the weak correlation to the one or more clusters.

2. The method of claim 1 where clustering comprises:
    modifying the analysis model into a standardized format;
    exporting the analysis model in the standardized format to a host production system that hosts models;
    applying the topic model to the EMR documents to identify one or more topics of content of each of the EMR documents in the host production system; and
    performing cluster analysis of the EMR documents using a vector derived from the topics of each of the EMR documents to produce the clusters, each including one or more cluster member ones of the EMR documents.

3. The method of claim 2 wherein applying the topic model comprises:
    identifying respective frequencies of one or more terms of the content of each of the EMR documents; and
    identifying the topics of the content of each of the EMR documents according to the frequencies of the terms.

4. The method of claim 3 wherein identifying respective frequencies comprises:
    comparing the frequencies of the terms to inverse document frequencies of the terms.

5. The method of claim 1 where training the EMR document analysis model comprises:
    for each of the clusters, determining a measure of correlation between the cluster and cluster member EMR documents of the cluster; and
    training a model to distinguish, for each of the clusters, cluster member EMR documents with high correlations with the cluster from cluster member EMR documents with low correlations with the cluster to produce the EMR analysis model.

6. The method of claim 1 wherein assigning EMR analysis labels to each of the sample EMR documents comprises:
    for each of the sample EMR documents:
    presenting the sample EMR document to one or more human analysts;
    prompting each of the analysts to associate either a positive label of the EMR analysis labels or a negative label of the EMR analysis labels to the sample EMR document, wherein the negative label is a logical inverse of the positive label;
    receiving label association data from each of the analysts, wherein the label association data indicates whether the positive label or the negative label is associated with the sample EMR document and is generated in response to physical manipulation of one or more user input devices by the analysts;
    determining whether the label association data represents that a predetermined minimum number of analysts associated the positive label with the sample EMR document or the predetermined minimum number of analysts associated the negative label with the sample EMR document; and
    associating the positive label with the sample EMR document upon a condition in which the predetermined minimum number of analysts associated the positive label with the sample EMR document or associating the negative label with the sample EMR document upon a condition in which the predetermined minimum number of analysts associated the negative label with the sample EMR document.

7. A non-transitory computer readable medium useful in association with a computer which includes one or more processors and a memory, the computer readable medium including computer instructions which are configured to cause the computer, by execution of the computer instructions in the one or more processors from the memory, to build an electronic medical record (EMR) document analysis model by at least:

collecting EMR documents from a database;
applying a latent Dirichlet allocation topic model to the EMR documents to generate cluster membership data comprising clusters associated with topics of the EMR documents, wherein one or more of the clusters comprises at least one thousand dimensions;
storing the cluster membership data as metadata associated with the EMR documents;
training the EMR document analysis model based on the clusters of the EMR documents and the metadata to produce a trained EMR document analysis model, wherein the clusters are based on the metadata and the topics associated therewith;
applying the trained EMR document analysis model to the EMR documents to produce adjusted cluster membership data for each of the EMR documents, the adjusted cluster membership data including a ranking associated with a respective distance of each of the EMR documents from a respective center of the one or more clusters, wherein being within a first distance from the respective center indicates strong correlation to the one or more clusters and a lower ranking, wherein being outside the first distance from the respective center indicates a weak correlation to the one or more clusters and a higher ranking;
updating the metadata based on the adjusted cluster membership;
receiving an input that identifies a condition or diagnosis;
creating labeled sample EMR documents by assigning EMR analysis labels associated with the condition or diagnosis to sample EMR documents, the sample EMR documents comprising EMR documents nearest a membership boundary of one or more of the clusters and outside the first distance from the respective center based on the updated metadata; and
training the trained EMR document analysis model with the labeled sample EMR documents to produce an improved EMR document analysis model with respect to the condition or diagnosis, thereby producing the improved EMR document analysis model based on training the trained EMR document analysis model with the labeled sample EMR documents indicating the weak correlation to the one or more clusters.

8. The computer readable medium of claim 7 where clustering comprises:
applying the topic model to the EMR documents to identify one or more topics of content of each of the EMR documents; and
performing cluster analysis of the EMR documents using a vector derived from the topics of each of the EMR documents to produce the clusters, each including one or more cluster member ones of the EMR documents.

9. The computer readable medium of claim 8 wherein applying the topic model comprises:
identifying respective frequencies of one or more terms of the content of each of the EMR documents; and
identifying the topics of the content of each of the EMR documents according to the frequencies of the terms.

10. The computer readable medium of claim 9 wherein identifying respective frequencies comprises:
comparing the frequencies of the terms to inverse document frequencies of the terms.

11. The computer readable medium of claim 7 where training the EMR document analysis model comprises:
for each of the clusters, determining a measure of correlation between the cluster and cluster member EMR documents of the cluster; and
training a model to distinguish, for each of the clusters, cluster member EMR documents with high correlations with the cluster from cluster member EMR documents with low correlations with the cluster to produce the EMR analysis model.

12. The computer readable medium of claim 7 wherein assigning EMR analysis labels to each of the sample EMR documents comprises, for each of the sample EMR documents:
presenting the sample EMR document to one or more human analysts;
prompting each of the analysts to associate either a positive label of the EMR analysis labels or a negative label of the EMR analysis labels to the sample EMR document, wherein the negative label is a logical inverse of the positive label;
receiving label association data from each of the analysts, wherein the label association data indicates whether the positive label or the negative label is associated with the sample EMR document and is generated in response to physical manipulation of one or more user input devices by the analysts;
determining whether the label association data represents that a predetermined minimum number of analysts associated the positive label with the sample EMR document or the predetermined minimum number of analysts associated the negative label with the sample EMR document; and
associating the positive label with the sample EMR document upon a condition in which the predetermined minimum number of analysts associated the positive label with the sample EMR document or associating the negative label with the sample EMR document upon a condition in which the predetermined minimum number of analysts associated the negative label with the sample EMR document.

13. A computer system comprising:
a processor;
a computer readable medium operatively coupled to the processor; and
EMR document analysis logic (i) that executes in the processor from the computer readable medium and (ii) that, when executed by the processor, causes the computer system to build an electronic medical record (EMR) document analysis model by at least:
collecting EMR documents from a database;
applying a latent Dirichlet allocation topic model to EMR documents to generate cluster membership data comprising clusters associated with topics of the EMR documents, wherein one or more of the clusters comprises at least one thousand dimensions;

storing the cluster membership data as metadata associated with the EMR documents;

training the EMR document analysis model based on the clusters of the EMR documents and the metadata to produce a trained EMR document analysis model, wherein the clusters are based on the metadata and the topics associated therewith;

applying the trained EMR document analysis model to the EMR documents to produce adjusted cluster membership data for each of the EMR documents, the adjusted cluster membership data including a ranking associated with a respective distance of each of the EMR documents from a respective center of the one or more clusters, wherein being within a first distance from the respective center indicates strong correlation to the one or more clusters and a lower ranking, wherein being outside the first distance from the respective center indicates a weak correlation to the one or more clusters and a higher ranking;

updating the metadata based on the adjusted cluster membership;

receiving an input that identifies a condition or diagnosis;

creating labeled sample EMR documents by assigning EMR analysis labels associated with the condition or diagnosis to the sample EMR documents, the sample EMR documents comprising EMR documents nearest a membership boundary of one or more of the clusters and outside the first distance from the respective center based on the updated metadata; and training the trained EMR document analysis model with the labeled sample EMR documents to produce an improved EMR document analysis model with respect to the condition or diagnosis, thereby producing the improved EMR document analysis model based on training the trained EMR document analysis model with the labeled sample EMR documents indicating the weak correlation to the one or more clusters.

14. The computer system of claim 13 where clustering comprises:

applying the topic model to the EMR documents to identify one or more topics of content of each of the EMR documents; and performing cluster analysis of the EMR documents using a vector derived from the topics of each of the EMR documents to produce the clusters, each including one or more cluster member ones of the EMR documents.

15. The computer system of claim 14 wherein applying the topic model comprises:

identifying respective frequencies of one or more terms of the content of each of the EMR documents; and identifying the topics of the content of each of the EMR documents according to the frequencies of the terms.

16. The computer system of claim 15 wherein identifying respective frequencies comprises:

comparing the frequencies of the terms to inverse document frequencies of the terms.

17. The computer system of claim 13 where training the EMR document analysis model comprises:

for each of the clusters, determining a measure of correlation between the cluster and cluster member EMR documents of the cluster; and training a model to distinguish, for each of the clusters, cluster member EMR documents with high correlations with the cluster from cluster member EMR documents with low correlations with the cluster to produce the EMR analysis model.

18. The computer system of claim 13 wherein assigning EMR analysis labels to each of the sample EMR documents comprises:

for each of the sample EMR documents:

presenting the sample EMR document to one or more human analysts;

prompting each of the analysts to associate either a positive label of the EMR analysis labels or a negative label of the EMR analysis labels to the sample EMR document, wherein the negative label is a logical inverse of the positive label;

receiving label association data from each of the analysts, wherein the label association data indicates whether the positive label or the negative label is associated with the sample EMR document and is generated in response to physical manipulation of one or more user input devices by the analysts;

determining whether the label association data represents that a predetermined minimum number of analysts associated the positive label with the sample EMR document or the predetermined minimum number of analysts associated the negative label with the sample EMR document; and associating the positive label with the sample EMR document upon a condition in which the predetermined minimum number of analysts associated the positive label with the sample EMR document or associating the negative label with the sample EMR document upon a condition in which the predetermined minimum number of analysts associated the negative label with the sample EMR document.

* * * * *